United States Patent [19]

Reichert et al.

[11] Patent Number: 5,556,844

[45] Date of Patent: Sep. 17, 1996

[54] PHARMACEUTICAL OR COSMETIC COMPOSITION CONTAINING A COMBINATION OF A RETINOID AND A STEROL

[75] Inventors: Uwe Reichert, Le Bar S/Loup; Rainer Schmidt, Mougins; Braham Shroot, Antibes, all of France

[73] Assignee: Centre International De Recherches Dermatologiques Galderma (Cird Galderma), Valbonne, France

[21] Appl. No.: 962,596

[22] PCT Filed: Jul. 2, 1991

[86] PCT No.: PCT/FR91/00526

§ 371 Date: Mar. 2, 1993

§ 102(e) Date: Mar. 2, 1993

[87] PCT Pub. No.: WO92/00076

PCT Pub. Date: Jan. 9, 1992

[30] Foreign Application Priority Data

Jul. 2, 1990 [FR] France .................................. 90 08344

[51] Int. Cl.⁶ ........................ A61K 31/07; A61K 31/20; A61K 31/235; A61K 31/575
[52] U.S. Cl. ..................... 514/171; 514/544; 514/560; 514/568; 514/703; 514/725

[58] Field of Search .................................. 514/171, 725, 514/560, 568, 544, 703

[56] References Cited

U.S. PATENT DOCUMENTS 4,961,922  10/1990  Shroot et al. ........................... 424/70

FOREIGN PATENT DOCUMENTS 0337890  10/1989  European Pat. Off. .

OTHER PUBLICATIONS

Jetten et al., J. Invest. Dermatol., 92(2), 203–209. 1989.
Ponec et al., Experimental Cell Research 171 (1987) 426–435.

*Primary Examiner*—Raymond Henley, III
*Assistant Examiner*—P. Spivack
*Attorney, Agent, or Firm*—Cushman Darby & Cushman, L.L.P.

[57] ABSTRACT

A pharmaceutical or cosmetic composition comprising in combination, a retinoid and a sterol inhibits the biosynthesis of cholesterol, is disclosed wherein a synergistic effect, principally in the treatment of disorders of epidermic keratinization, disorders of epidermic or epithelial proliferation and/or disorders of sebaceous function, is exhibited.

23 Claims, No Drawings

PHARMACEUTICAL OR COSMETIC COMPOSITION CONTAINING A COMBINATION OF A RETINOID AND A STEROL

The present invention has for an object a pharmaceutical or cosmetic composition having a synergistic effect, intended principally for the treatment of epidermic keratinization disorders, epithelial or epidermic proliferation disorders, and/or disorders of the sebaceous function, the said composition comprising, in combination, at least one retinoid and at least one steroid that inhibits the biosynthesis of cholesterol.

It is known that agents controlling cellular differentiation, such as retinoids, are largely employed or envisioned for the treatment of keratinization disorders. These retinoids have principally the property of inhibiting the formation of cornified envelopes (CE) of the epidermis, that is to say, the last phase of the differentiation of keratinocytes. The mechanism of biological activity involved is known: it is a question of an inhibition of the expression of membranal transglutaminase (TGm) which is an essential enzyme in the synthesis of CE; see for example FEBS LETTERS, Vol. 258, No. 1, p. 35–38 (1989), Vol. 229 No. 1, p. 193–196 (1988) and Vol. 186, No. 2, p. 201–204 (1985), and J. Invest. Dermatol. Vol. 90, No. 4, p. 472–474 (1988).

It is also known that 25-hydroxy cholesterol is also capable of inhibiting the synthesis of CEs; see principally Exp. Cell. Res. 171, p. 426–435 (1987).

It has now been discovered that the inhibition of the synthesis of cornified envelopes by 25-hydroxy cholesterol results from a different biochemical mechanism: it is a question of an inhibition of the biosynthesis of cholesterol.

It has also been discovered that compositions containing, in combination, both a retinoid capable of inhibiting the expression of TGm and a sterol capable of inhibiting the biosynthesis of cholesterol exhibits a synergistic effect in that which concerns the inhibition of the synthesis of CEs.

These two types of compounds act by two independent biochemical ways, and it would normally be expected, with the combination, to obtain a resultant inhibiting activity of the synthesis of the CEs equal to the addition of the activities obtained with the compounds tested separately. However, it has now been discovered, in a surprising manner, that the combination mentioned above causes a synergism: the level of inhibition obtained is very sharply superior to the addition of the inhibitions due to the constituents of the combination taken separately.

The present invention has for an object a synergistic composition resulting from the combination of two agents controlling cellular differentiation by mechanisms of different activity, to treat or correct epidermic keratinization disorders, any other disorder or any other functions defect or excess of the epidermic or epithelial proliferation and/or disorders of the sebaceous function, accompanied or not by an inflammatory and/or immunoallergic component. The composition of the invention permits, for example, to treat conjunctive tissue degeneration diseases, benign or malignant tumors, to combat against skin aging, to favor cicatrization, or even to improve the appearance of the skin of persons exhibiting keratinization disorders.

The combination, according to the present invention, also finds use in the ophthalmologic field, principally in the treatment of corneopathies.

The use of this combination provides principally the advantage of permitting to obtain a sufficient activity all while sharply reducing the amount of the agent controlling cellular differentiation and, consequently, limiting or even suppressing, secondary effects due to this agent. There can thus be employed, for example, a compound having an activity of the retinoid type which is much less powerful, and consequently less toxic, than that of retinoic acid, and obtain however, thanks to the synergism, an equivalent activity.

The pharmaceutical or cosmetic composition having a synergistic effect of the invention comprises then, in combination, at least one retinoid capable of inhibiting the expression of TGm, and at least one sterol that inhibits the biosynthesis of cholesterol.

The retinoids constitute a class of known compounds, which comprise vitamin A, its natural derivatives and all synthetic derivatives having an affinity for nuclear receptors of retinoic acid; see, for example, Nouv. Dermatol. 9.1, 3–6 (1990).

By "retinoids" is meant compounds which respond to this definition, and, in particular, retinoic acid and its derivatives, and also various analogs which are mentioned below.

The retinoids useful in the composition of the present invention are those which are capable of inhibiting the expression of TGm, for example, in accordance with the test described by S. Michel et al, in Models Dermatol., Maibach and Lowe Eds., Karger, Basel Vol. 4, p. 40–44 (1989).

Among the retinoids or products having an activity of the retinoid type, useful in the compositions of the present invention, mention can principally be made of, the following derivatives, as well as their esters and their amides:

all trans or 13-cis retinoic acid, vitamin A or retinol, as well as its esters such as the acetate, propionate or palmitate of retinol, the aldehyde of vitamin A or retinal, (all-E)-9-(4-methoxy-2,3,6-trimethylphenyl)-3,7-dimethyl-2,4,6,8-nonatetraenoic acid (acitreten), (E,E,E)-7-(2,3,-dihydro-1,1,3,3-tetramethyl-1H-inden-5-yl)-3,7-dimethyl-2,4,6-octatrienoic acid, (E,E,E)-7-(5,6,7,8-tetrahydro-5,5,8,8-tetramethyl-2-naphthalenyl)- 3,7-dimethyl-2,4,6-octatrienoic acid, (E)-4-[(2,3,-dihydro-1,1,3,3-tetramethyl-1H-inden-5-yl)-1-propenyl] benzoic acid, (E)-4-[2-(5,6,7,8-tetrahydro-5,5,8,8-tetramethyl-2-naphthalenyl)- 1-propenyl] benzoic acid, (E)-4-[2-(5,6,7,8-tetrahydro-3-methyl-5,5,8,8-tetramethyl-2-naphthalenyl)-1-propenyl] benzoic acid, 2-(5,6,7,8-tetrahydro-5,5,8,8-tetramethyl-2-naphthyl)-6-naphthalene carboxylic acid, (E)-4-[2-(5,6,7,8-tetrahydro-5,5,8,8-tetramethyl-2-naphthalenyl)- 1-propenyl] benzene sulfonic acid, (E,E)-4-[2-methyl-4-(2,6,6-trimethyl-1-cyclohexen-1-yl)-1,3-butadienyl] benzoic acid, (E,E)-4-[4-methyl-6-(2,6,6-trimethyl-1-cyclohexen-1-yl)-1,3,5-hexatrienyl] benzoic acid, (E)-6-[2-(2,6,6-trimethyl-1-cyclohexen-1-yl)-ethenyl]-2-naphthalene carboxylic acid, (E,E)-5-[2-methyl-4-(2,6,6-trimethyl-1-cyclohexen-1-yl)-1,3-butadienyl]-2-thiophene carboxylic acid, (E)-4-[2-(5,6,7,8-tetrahydro-8,8-dimethyl-2-naphthalenyl)-1-propenyl] benzoic acid, 4-[(5,6,7,8-tetrahydro-5,5,8,8-tetramethyl-2-naphthenyl)ethynyl] benzoic acid, 4-(5,6,7,8-tetrahydro-5,5,8,8-tetramethyl-2-naphthalenylcarbamoyl) benzoic acid, 4-(5,6,7,8-tetrahydro-5,5,8,8-tetramethyl-2-naphthamido) benzoic acid, (E)-4-[3-(3,5-ditert-butylphenyl)-3-oxo-1-propenyl] benzoic acid, 6-[(5,6,7,8-tetrahydro-5,5,8,8-tetramethyl-2-naphthalenyl) ethynyl] 3-pyridine carboxylic acid.

Mention can also be made of the following derivatives: aromatic heterocyclic retinoids described in French patent 85.13747 (FR 2570377) such as:

2-(5,6,7,8-tetrahydro-5,5,8,8-tetramethyl-2-naphthyl)-6-benzo(b) thiophene carboxylic acid, 2-(5,6,7,8-tetrahydro-5,5,8,8-tetramethyl-2-naphthyl)-6-benzo(b) furane carboxylic acid, 2-(5,6,7,8-tetrahydro-5,5,8,8-tetramethyl-2-naphthyl)-6-indole carboxylic acid, 2-[3-(1-adamantyl)-4-methoxyphenyl]-5-benzimidazole carboxylic acid, 2-(5,6,7,8-tetrahydro-5,5,8,8-tetramethyl-2-naphthyl)-5-benzimidazole carboxylic acid, the polycyclic aromatic retinoids described in EP patent application 0 210 929 such as:

4-(5,6,7,8-tetrahydro-5,5,8,8-tetramethyl-2-anthracenyl) benzoic acid;

the benzonaphthalenic retinoids described in EP patent application 0 199 636, as for example:

6-[3-(1-adamantyl)-4-methoxyphenyl]-2-naphthoic acid;

the aromatic benzamido retinoids described in EP patent application 0 232 199 as, for example:

4-[3-(1-adamantyl)-4-methoxybenzamido] benzoic acid;

the aromatic benzoyloxythio retinoids described in EP patent application 0 325 540 such as:

4-[3-(1-adamantyl)-4-methoxy benzoylthio] benzoic acid or

4-[3-(1-adamantyl)-4-methoxy benzoyloxy] benzoic acid;

the naphthalenic bicyclic retinoids described in EP patent application 0 220 118, for example:

2-(5,6,7,8-tetrahydro-5,5,8,8-tetramethyl-2-naphthyl)-6-carbonyl naphthalene carboxylic acid;

the aromatic bicyclic retinoids described in French patent 87-06152 (2 614 618) as for example:

p-(5,6,7,8-tetrahydro-5,5,8,8-tetramethyl-2-1H-benz[f] indolyl) benzoic acid;

the aromatic bicyclic retinoids described in French patent 86 10423 (2 601 670), for example:

trans-(5,5,8,8-tetramethyl-5,6,7,8-tetrahydro-2-naphthyl)-4-carbonyl-α-methyl cinnamic acid;

the bi-aromatic retinoid esters described in EP patent application 90-402072, having the general formula:

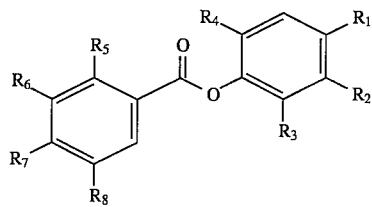

wherein $R_1$ represents hydrogen, OH, —CH$_3$, —CH$_2$OH, —CH(OH)CH$_3$, —COOR$_9$,

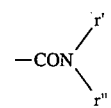

or SO$_2$R$_{10}$, $R_9$ represents hydrogen, alkyl having 1–6 carbon atoms or a mono or polyhydroxyalkyl, $R_{10}$ represents OH, alkyl having 1–6 carbon atoms or

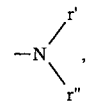

r' and r" represent hydrogen, alkyl having 1–6 carbon atoms, aryl, aralkyl, mono or polyhydroxyalkyl, or r' and r" taken together form a heterocycle, $R_2$ represents hydrogen, alkyl having 1–6 carbon atoms, OR$_9$, a fluorine or —CF$_3$, $R_3$, $R_4$ and $R_5$ represent hydrogen, a fluorine atom, OH, —CH$_3$, —OCH$_3$, CF$_3$, —COOH or —CH$_2$OH, $R_6$ and $R_8$ represent hydrogen, α-substituted alkyl having 3–15 carbon atoms, α,α'-disubstituted alkyl having 4–12 carbon atoms, cycloalkyl having 3–12 carbon atoms, mono or polycyclic cycloalkyl having 5–12 carbon atoms, the linking carbon atom of which is trisubstituted, —SR$_{11}$, —SO$_2$R$_{11}$ or —SOR$_{11}$, $R_{11}$ represents alkyl having 1–6 carbon atoms or cycloalkyl, $R_6$ and $R_8$ not simultaneously representing hydrogen, $R_7$ represents hydrogen, alkyl having 1–6 carbon atoms, alkenyl, alkenyloxy, OR$_{12}$, SR$_{13}$, SOR$_{14}$ or SO$_2$R$_{14}$, $R_{12}$ represents hydrogen, alkyl having 1–6 carbon atoms, alkenyl, mono or polyhydroxy alkyl or —(CH$_2$)$_n$—COR$_{15}$, n is 0, 1 or 2 and $R_{15}$ represents hydrogen, OH, alkyl having 1–6 carbon atoms or alkoxy having 1–6 carbon atoms, $R_{13}$ represents hydrogen, alkyl having 1–6 carbon atoms or aralkyl, $R_{14}$ represents OH, alkyl having 1–6 carbon atoms or aralkyl, with the proviso that when $R_1$ represents —CH$_2$OH, —CH(OH)CH$_3$, —COOR$_9$ or

and $R_2$ represents hydrogen then:
(i) either $R_3$ and $R_4$ are other than hydrogen or —CH$_3$,
(ii) or $R_7$ is other than OR$_{12}$ and $R_6$ or $R_8$ is cycloalkyl having more than 7 carbon atoms,
(iii) or $R_7$ represents OR$_{12}$, but $R_6$ and $R_8$ are then other than hydrogen,
(iv) or $R_7$ represents OR$_{12}$, but then $R_5$ is other than hydrogen, and in particular:
   4-[3-(1-adamantyl)-4-methoxybenzoyloxy]-2-fluorobenzoic acid,
   4-[3-(1-adamantyl)-4-methoxybenzoyloxy]-2-methylbenzoic acid,
   4-[3(1 adamantyl)-4-methoxybenzoyloxy]-2-hydroxybenzoic acid, 4-[5-(1-adamantyl)-2-fluoro-4-methoxybenzoyloxy] benzoic acid, 4-[3,5-di-tert. butyl-4-hydroxybenzoyloxy] benzoic acid, 4-[3-(1-adamantyl)-4-vinylbenzoyloxy] benzoic acid, 4-[3-(1-adamantyl)-4-ethylbenzoyloxy] benzoic acid, 4-[3-(1-adamantyl)-4-allyloxybenzoyloxy] benzoic acid, 4-[3-(1-adamantyl-4-methylthiobenzoyloxy] benzoic acid;

the bi-aromatic retinoids described in Luxembourg application 87 821 having the general formula I

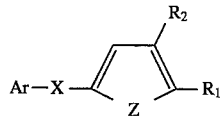

(I)

wherein

Ar represents either the radical

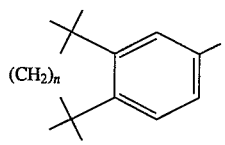

(II)

wherein n=1 or 2 or the radical

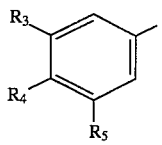

(III)

wherein $R_3$ and $R_5$ represent hydrogen, OH, alkoxy having 1–6 carbon atoms, α-substituted alkyl having 3–12 carbon atoms or α,α'-disubstituted alkyl having 4–12 carbon atoms, cycloalkyl having 3–12 carbon atoms, mono or polycyclic cycloalkyl having 5–12 carbon atoms whose linking carbon is trisubstituted, $R_4$ represents hydrogen, OH, alkoxy having 1–6 carbon atoms, α-substituted alkyl having 3–12 carbon atoms, α,α'-disubstituted alkyl having 4–12 carbon atoms, cycloalkyl having 3–12 carbon atoms, mono or polycyclic cycloalkyl having 5–12 carbon atoms whose linking carbon is trisubstituted, monohydroxyalkyl, polyhydroxyalkyl, fluorine, chlorine, SH, $SR_6$, $SOR_6$, $SO_2R_6$, alkenyl having 2–6 carbon atoms or alkenyloxy having 2–6 carbon atoms, $R_6$ represents lower alkyl, $R_1$ represents hydrogen, OH, —CH$_3$, —CH$_2$OH, —COR$_7$, —CH(OH)CH$_3$, —CH$_2$OCOR$_8$, —SO$_2$R$_9$, —SOR$_9$ or —SR$_9$, $R_7$ represents hydrogen, OH, —OR$_{10}$, —N(r'r''), lower alkyl, monohydroxyalkyl, polhydroxyalkyl or a sugar residue, $R_{10}$ represents alkyl having 1–12 carbon atoms or alkenyl having 2–12 carbon atoms, r' and r'', each independently, represent hydrogen, lower alkyl, aryl, aralkyl, the residue of an amino acid, a sugar residue, an aminated sugar residue, or a heterocycle where r' and r'' taken together form a heterocycle, $R_8$ represents linear or branched, saturated or unsaturated alkyl having 1–20 carbon atoms or a sugar residue, $R_9$ represents OH, lower alkyl or —N(r'r''), $R_2$ represents hydrogen, OH, lower alkyl, alkoxy having 1–6 carbon atoms, fluorine, chlorine, CF$_3$, COR$_7$, CH$_2$OH or CH$_2$OR$_6$, Z represents oxygen or sulfur, —CH═CR$_{11}$—, —N═CH—, —N═CR$_6$, R$_{11}$ represents hydrogen, OH, lower alkyl, alkoxy having 1–6 carbon atoms, fluorine, chlorine or CF$_3$, X is a divalent radical that can be read left to right or inversely, selected from the group consisting of:

(i) 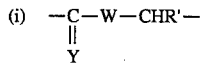

wherein

R' represents hydrogen or —CH$_3$,

W represents an atom of oxygen or sulfur or —NR', and

Y represents an atom of oxygen or even an atom of sulfur when W represents —NR', (ii) 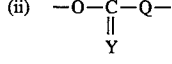

wherein

Q represents an atom of oxygen or —NR',

Y represents an atom of oxygen or even an atom of sulfur when Q represents —NR', (iii) 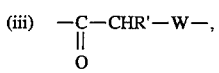

(iv) 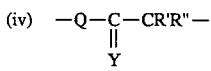

wherein

R'' represents hydrogen, —CH$_3$, OH, an atom of fluorine or an atom of chlorine, or R' and R'' taken together form a methano (═CH$_2$) radical or an oxo (═O) radical, (v) 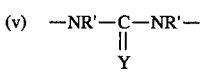

wherein

Y represents an atom of oxygen or an atom of sulfur, and the salts of the compounds of formula (I) when R$_1$ represents a carboxylic acid function and the optical isomers of the said compounds of formula (I), and, in particular 4-(5,6,7,8,-tetrahydro-5,5,8,8-tetramethyl-2-naphthylglyoxyloyloxy) benzoic acid, 4-(5,6,7,8-tetrahydro-5,5,8,8-tetramethyl-2-naphthoyloxymethyl) benzoic acid, 4-(3,5-di-tert.butyl-4-hydroxybenzoyloxymethyl) benzoic acid, 4-(3-tert.butyl-4-methoxybenzoyloxymethyl) benzoic acid, 5-(5,6,7,8-tetrahydro-5,5,8,8-tetramethyl-2-naphthoyloxymethyl)- 2-thiophene carboxylic acid, 4-(5,6,7,8-tetrahydro-5,5,8,8-tetramethyl-2-naphthoylmethyloxy) benzoic acid, 4-[1-(5,6,7,8-tetrahydro-5,5,8,8-tetramethyl-2-naphthoyloxy) ethyl] benzoic acid, 4-[[(5,6,7,8-tetrahydro-5,5,8,8-tetramethyl-2naphthyl)ethyloxy] carbonyl] benzoic acid, 4-(5,6,7,8-tetrahydro-5,5,8,8-tetramethyl-2-naphthoylm-
ethylamino)benzoic acid, 4-(5,6,7,8-tetrahydro-5,5,8,8-tetramethyl-2-naphthoyl
formamido)benzoic acid, 4-(α-hydroxy-5,6,7,8-tetrahydro-5,5,8,8-tetramethyl-2-
naphthylacetamido) benzoic acid and 4-(α-fluoro-5,6,7,8-tetrahydro-5,5,8,8-tetramethyl-2-
naphthylacetamido) benzoic acid.

Various reaction schemes can be considered in obtaining these compounds of formula (I), in the case where Y is an atom of oxygen.

Mention can be made of the following reaction schemes:
In the case where X is either (i) or (iv),

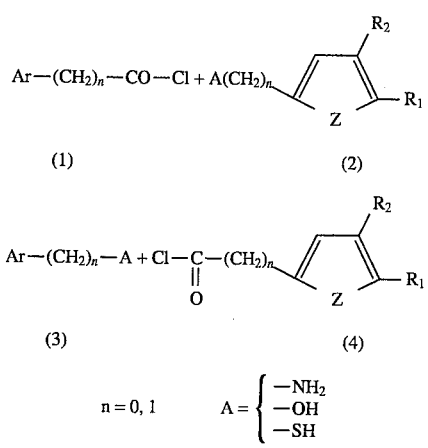

$$n = 0, 1 \quad A = \begin{cases} -NH_2 \\ -OH \\ -SH \end{cases}$$

The principal step in this preparation consists in reacting in an anhydrous medium, in an organic solvent such as tetrahydrofuran or methylene chloride containing a tertiary amine (triethylamine) or pyridine or an alkaline hydride (sodium hydride), an activated form of a substituted aromatic acid or an arylacetic acid substituted by, for example, an acid chloride (1) or (4) or a mixed anhydride, or an aromatic compound having a hydroxy function or amino or thiol (2) or (3), the reaction being effected at ambient temperature and with stirring.

When $R_1$ represents —COOH, the compounds are prepared by protecting $R_1$ with a protective group of the allylic, benzylic or tert. butylic type.

Passage to the free form can be effected:
  in the case of an allylic protective group, by means of a catalyst such as certain transition metal complexes in the presence of a secondary amine;
  in the case of a benzylic protective group, by debenzylation in the presence of hydrogen, by means of a catalyst such as palladium on charcoal; and
  in the case of a tert. butylic protective group, by means of trimethylsilyl iodide.

In the case where X is either (ii) or (v):

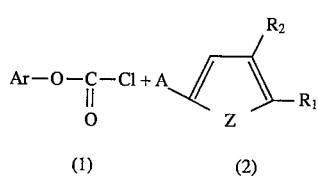

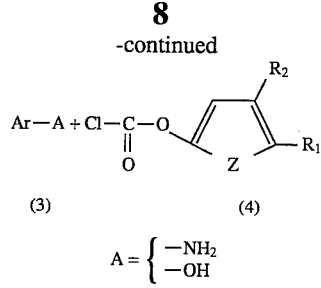

$$A = \begin{cases} -NH_2 \\ -OH \end{cases}$$

The principal step in this preparation consists in reacting in an anhydrous medium, in an organic solvent such as methylene chloride, containing a tertiary amine (triethylamine) or pyridine, a chloroformate (1) or (4) prepared, for example, starting with a hydroxyaryl derivative and trichloromethyl chloroformate or phosgene, with an aromatic compound having a hydroxy or amino (2) or (3) function. The reaction is carried out at ambient temperature and with stirring.

In the case where $R_1$ represents —COOH, the compounds are prepared, preferably, by protecting $R_1$ with a benzylic protective group. Passage to the free form is effected by debenzylation in the presence of hydrogen, by means of a catalyst such as palladium on charcoal.

In the case where X is (iii) and if Z is not an atom of oxygen,

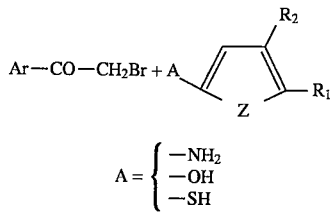

$$A = \begin{cases} -NH_2 \\ -OH \\ -SH \end{cases}$$

The principal step in this preparation consists in reacting in the presence of potassium carbonate or an alkaline hydride (sodium hydride) or by phase transfer by using, for example, tetrabutylammonium bromide as a quaternary ammonium salt, an aromatic alpha-bromoketone with an aromatic compound having a hydroxy or amino or thiol function para to the $R_1$ radical.

In the case where $R_1$ represents —COOH, the compounds are prepared preferably by protecting $R_1$ by an allylic protective group. Passage to the free form is effected by means of a catalyst such as trakis (triphenylphosphine) palladium (O) in the presence of a secondary amine (morpholine).

The acids thus obtained can be converted, in a known manner, into a corresponding acid chloride which, treated with an ($R_6$OH) alcohol or an HN (r')(r") amine gives the corresponding ester or amide;

the aromatic polycyclic retinoids described in French patent application 91-05394, having the general formula (IV):

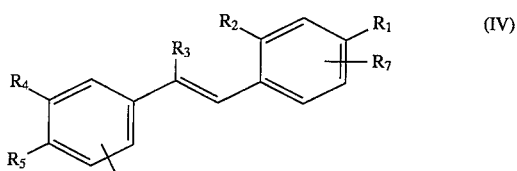

wherein
$R_1$ represents (i) an atom of hydrogen,
(ii) —CH₃,
(iii) —CH₂—O—R₈, wherein R₈ represents hydrogen or lower alkyl,
(iv) —OR₈,
(v)

wherein R₁₀ represents (a) hydrogen, (b)

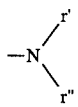

wherein r' and r" represent hydrogen, lower alkyl, mono or polyhydroxyalkyl, aryl optionally substituted or the residue of an amino acid or a sugar, or even taken together form a heterocycle, (c) —OR₁₁, wherein R₁₁ represents hydrogen, linear or branched alkyl having 1–20 carbon atoms, mono or polyhydroxyalkyl, aryl or aralkyl optionally substituted or a sugar residue or an amino acid residue,
(vi) —S(O)ₜR₈, wherein t is 0, 1 or 2 and R₈ is defined above, and
(vii)

wherein R₈ is defined above,
R₂ represents hydrogen,
R₃ represents hydrogen, aryl, aralkyl or lower alkyl optionally substituted by hydroxyl, by a lower alkoxy or by

R₁₂ represents hydrogen, lower alkyl, hydroxyl, lower alkoxy

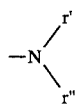

wherein r' and r" have the meanings given above, or R₂ and R₃ taken together form, with the benzene ring, a naphthalenic ring,
R₄ represents a linear or branched alkyl having 1–15 carbon atoms or a cycloaliphatic radical,
R₅ represents —(CH₂)ₙ—R₁₃, —CH=CH—(CH₂)ₙ—R₁₃ or —O (CH₂)ₘR₁₄, wherein n is 0 or 1–6, m is 1–6,
R₁₃ represents

monohydroxyalkyl or polyhydroxyalkyl whose hydroxyl groups are Optionally protected under methoxy or acetoxy form, epoxidized lower alkyl or

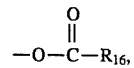

R₁₅ represents OR₁₆ or

R₁₆ represents hydrogen, lower alkyl, aryl or aralkyl,
R₁₄ represents hydroxyl when m≧2, monohydroxyalkyl, polyhydroxyalkyl,

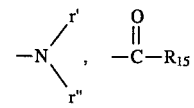

or a mono or polyhydroxylated alkenyl having 2–10 carbon atoms, or when R₂ and R₃ are not taken together, m can be 0 and/or R₁₄ can represent hydrogen or lower alkyl,
R₆ and R₇ represent hydrogen, halogen, lower alkyl or —OR₁₆,
R₅ and R₆ can also form a methylenedioxy ring when R₆ is in position 3 of the benzene ring,
and the salts of the compounds of formula (IV) when R₁ or R₁₃ represent a carboxylic acid function or when R₁₄ represents an amine function and the chiral analogs of the said compounds of formula (IV), and in particular:
  6-[3-(1-adamantyl)-4-(2,3-dihydroxypropyloxy) phenyl]-2-naphthoic acid,
  6-[3-(1-adamantyl)-4-(3-hydroxypropyloxy)phenyl]-2-naphthoic acid,
  6-[3-(1-adamantyl)-4-acetoxymethylphenyl]-2-naphthoic acid,
  6-[3-(1-adamantyl)-4-methoxycarbonylphenyl]-2-naphthoic acid,
  6-[3-(1-adamantyl)-4-methoxycarbonylethylphenyl]-2-naphthoic acid and
  6-[3-(1-adamantyl)-4-(2-hydroxypropyl) phenyl]-2-naphthoic acid.

The compounds of formula (IV) for which R₂ and R₃ taken together form with the benzenic nucleus a naphthalenic ring are obtained by the coupling reaction between a halogen derivative (1) and a halogen derivative of formula (2):

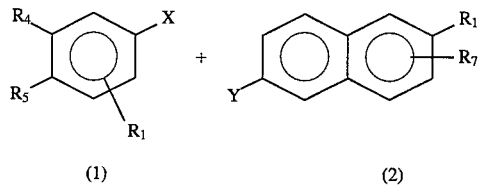

wherein
  X and Y represent an atom of chlorine, bromine or fluorine.

In a first stage, the halide (1) is converted into a lithia, magnesia or zinc compound and then is coupled with derivative (2) in the presence of a catalyst with nickel or palladium, according to the biaryl coupling conditions described by E. Negishi et al., J. Org. Chem. (1977) 42, 1821.

The compounds of formula (IV) for which $R_2$ and $R_3$ are not taken together can be obtained by the following reaction scheme by putting into play a Wittig or Horner-Emmons reaction.

Under these olefination reaction, the geometric isomer of configuration E can also be obtained by conversion under irradiation by UV light of the isomer of geometric configuration Z.

In these formulas $R_1$, $R_4$, $R_6$ and $R_7$ have the same meanings as those given above for the general formula or are derivatives suitably protected to be compatible with the coupling conditions. In particular the substituent $R_5$ is a phenol protected in the form of tert. butyldimethylsilyloxy or an alkoxy radical.

The resulting derivative is then converted into phenol by deprotection at the substituent $R_5$ of the TBDMS or alkoxy group and then is treated according to one of the two ways mentioned below:

treatment of the phenol thus obtained by a metallic hydride that one reacts on a halide; or conversion of the phenol thus obtained into triflate, then nucleophic substitution in the presence of a catalyst with palladium;

the bi-aromatic retinoid derivatives having a salicylic unit described in French patent application 91-05747 of the following general formula (V):

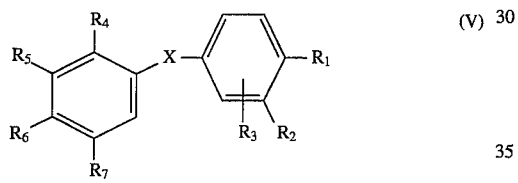

wherein $R_1$ represents —$CH_3$, —$CH_2OH$, —$COR_8$ or —$CH_2OCOR_9$, $R_8$ represents hydrogen, OH, —$OR_{10}$,

or lower alkyl, $R_{10}$ represent alkyl having 1–20 carbon atoms, alkenyl having 2–20 carbon atoms, aryl or aralkyl, r and r', each independently, represent hydrogen, lower alkyl, aryl, aralkyl, a residue of an amino acid, a sugar residue or a heterocycle when r and r' taken together form a heterocycle, $R_9$ represents alkyl having 1–20 carbon atoms, alkenyl having 2–20 carbon atoms or a sugar residue, $R_2$ and $R_3$ represent —$OR_{11}$ or —$OCOR_{11}$, $R_{11}$ represents hydrogen, lower alkyl, fluoroalkyl having 1–6 carbon atoms and 3–7 fluorine atoms, aryl or aralkyl, $R_3$ can also represent hydrogen, $R_4$ represents hydrogen, OH, lower alkyl, alkoxy having 1–6 carbon atoms, an atom of fluorine, chlorine or —$CF_3$, $R_5$ and $R_7$ represent hydrogen, OH, alkoxy having 1–6 carbon atoms, α-substituted alkyl having 3–12 carbon atoms or α,α'-disubstituted alkyl having 4–12 carbon atoms, cycloalkyl having 3–12 carbon atoms, a mono or polycyclic radical having 5–12 carbon atoms linked to the phenyl nucleus by a tertiary carbon, $R_6$ represents hydrogen, OH, lower alkyl, alkoxy having 1–6 carbon atoms, cycloalkyl having 3–12 carbon atoms, monohydroxyalkyl, polyhydroxyalkyl, fluorine, chlorine, alkenyl having 2–6 carbon atoms or alkenyloxy having 2–6 carbon atoms, $R_5$ and $R_6$ or $R_6$ and $R_7$, taken together can form with the adjacent aromatic ring a ring having 5 or 6 chains optionally substituted by methyl groups and/or optionally interrupted by an atom of oxygen or sulfur, X is a divalent radical that can be read left to right or inversely and selected from the group consisting of
(i) —$C(R_{13}R_{14})$—$C(R_{16}R_{18})$—W—,
(ii) —$C(R_{14}R_{16})$—W—$C(R_{18}R_{19})$—,
(iii) —$C(R_{13}R_{14})$—$C(R_{15}R_{16})$—$C(R_{18}R_{20})$— and
(iv) —$CR_{17}$=$CR_{21}$—$C(R_{13}R_{14})$—
wherein W represents oxygen, —$NR_{12}$ or $S(O)_n$ wherein n is 0, 1 or 2, $R_{13}$, $R_{15}$ and $R_{20}$ represent hydrogen, —$OR_{11}$, —$OCOR_{11}$, —$NHCOR_{11}$,

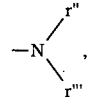

aralkyl, lower alkyl, monohydroxyalkyl or or polyhydroxyalkyl, r" and r''', each independently, represent hydrogen, lower alkyl, alkenyl having 2–6 carbon atoms or alkynyl having 2–6 carbon atoms, $R_{14}$, $R_{16}$, $R_{18}$ and $R_{19}$ represent hydrogen, aralkyl, lower alkyl, monohydroxyalkyl or polyhydroxyalkyl, when X represents (i), $R_{13}$ and $R_{14}$ can form a =N—$OR_{11}$ or an =N—$OCOR_{11}$ group, when X represents (iii) or (iv), $R_{14}$, $R_{16}$ and $R_{18}$ can also represent —$OR_{11}$ or —$OCOR_{11}$, or $R_{13}$, $R_{14}$ and/or $R_{15}$, $R_{16}$ or again $R_{13}$, $R_{14}$ and $R_{18}$, $R_{20}$ taken together can form an oxo group, or $R_{13}$, $R_{14}$ or $R_{15}$, $R_{16}$ taken together can form an =$NOR_{11}$ or =N—$OCOR_{11}$ group, $R_{12}$ represents hydrogen, lower alkyl, aralkyl, alkenyl having 2–6 carbon atoms, alkynyl having 2–6 carbon atoms or fluoroalkyl having 1–6 carbon atoms and 3–7 fluorine atoms, $R_{17}$ represents hydrogen, hydroxyl, lower alkyl or alkoxy having 1–6 carbon atoms, $R_{21}$ represents hydrogen or lower alkyl, and the salts of the compounds of formula (V) when $R_1$ represents a carboxylic acid function or when $R_{13}$, $R_{16}$ or $R_{20}$ represent an amine function and the optical isomers of the compounds of formula (V) and in particular:

2-hydroxy-4-[2-hydroxy-2-(5,6,7,8-tetrahydro-5,5,8,8-tetramethyl- 2-naphthyl) ethoxy] benzoic acid, methyl 2-hydroxy-4-[2-hydroxy-2-(5,6,7,8,-tetrahydro-5, 5,8,8-tetramethyl-2-naphthyl) ethoxy] benzoate, 2-hydroxy-4-[2-hydroxyimino-2-(5,6,7,8-tetrahydro-5,5, 8,8-tetramethyl- 2-naphthyl) ethoxy]benzoic acid, 2-acetyloxy-4-[2-acetyloxy-2-(5,6,7,8-tetrahydro-5,5,8, 8-tetramethyl- 2-naphthyl) ethoxy] benzoic acid, 2-hydroxy-4-[2-acetyloxy-2-(5,6,7,8-tetrahydro-5,5,8,8-tetramethyl- 2-naphthyl) ethoxy] benzoic acid and 2-acetyloxy-4-[2-hydroxy-2-(5,6,7,8-tetrahydro-5,5,8,8-tetramethyl- 2-naphthyl) ethoxy] benzoic acid.

The compounds of formula (V), and in particular those of formulas (Va), (Vb), (Vc), (Vd) and (Ve), given below, can be prepared in accordance with the following reaction schemes:

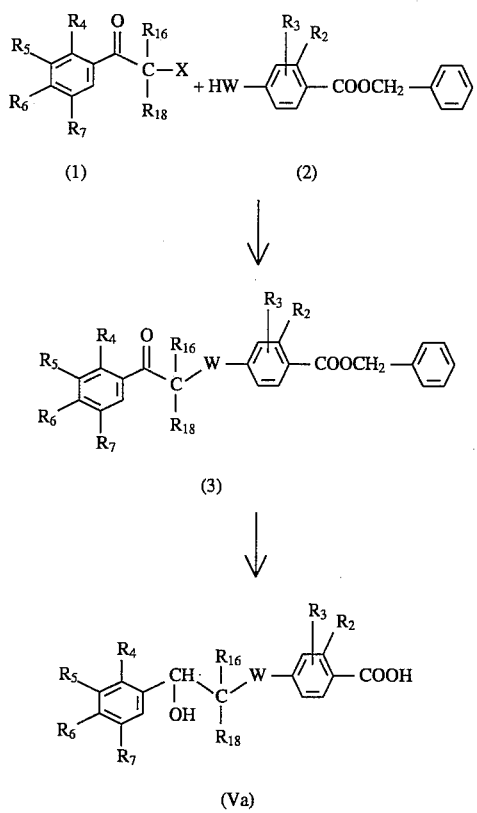

The first step in this preparation consists in reacting in an anhydrous medium, in an organic solvent such as DMF, an α-halide (1) with a benzyl parahydroxy, paramino or parathiosalicylate (2) in the presence of a tertiary amine (pyridine or triethylamine) or an alkaline hydride (sodium hydride) to obtain the compound of formula (3).

The principal step consists in hydrogenating the compound of formula (3) in the presence of a catalyst such as palladium on charcoal in an organic solvent such as dioxane, methanol or THF.

Hydrogenation can be effected at a temperature between 20° and 60° C. under a hydrogen pressure between 1 bar and 7 bars and permits at the same time to obtain the free acid and to reduce the ketonic function.

By the hydroxylamine action on compound (3), a hydroximino is obtained. The reduction of the hydroximino permits to obtain the corresponding aminated compound.

The compounds of general formula (V) where X is (i) can also be prepared by the action of an acid chloride (5) with an aromatic derivative (4) in the presence of a Lewis acid (for example, $AlCl_3$) in a chlorinated solvent such as dichloromethane, dichloroethane, or nitrated solvent such as nitromethane, nitrobenzene. The ketone (6) thus obtained is reduced in alcohol with an alkaline hydride such as $NaBH_4$ in an organic solvent such as THF, or ethanol:

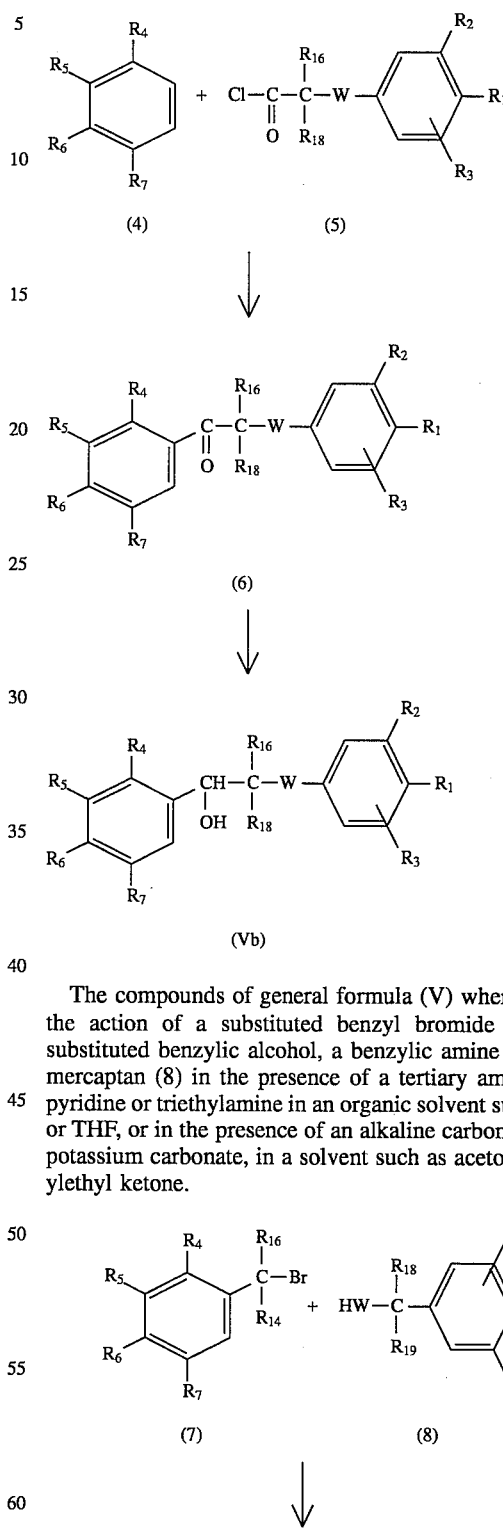

The compounds of general formula (V) where X=(ii) by the action of a substituted benzyl bromide (7) with a substituted benzylic alcohol, a benzylic amine or benzylic mercaptan (8) in the presence of a tertiary amine such as pyridine or triethylamine in an organic solvent such as DMF or THF, or in the presence of an alkaline carbonate, such as potassium carbonate, in a solvent such as acetone or methylethyl ketone.

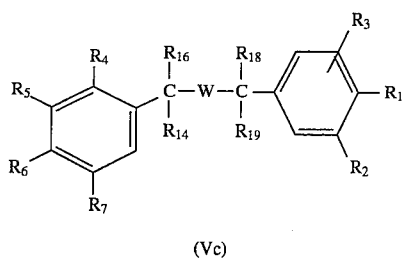

(Vc)

The compounds of general formula (V) where X=(iv) can be prepared by the action of a substituted acetophenone (9) with a substituted benzaldehyde (10) in the presence of a base such as soda or sodium methylate in an alcoholic solvent (ethanol). The chalcone (11) thus obtained is reduced in an allylic alcohol (Vd) using an alkaline hydride such as $NaBH_4$ in an alcoholic solvent in the presence of a catalyst ($CeCl_3$).

By hydrogenation of the compound (Vd) in the presence of a catalyst such as palladium on charcoal in a solvent such as dioxane or methanol compounds (Ve) of general formula (V) where X=(iii) are obtained.

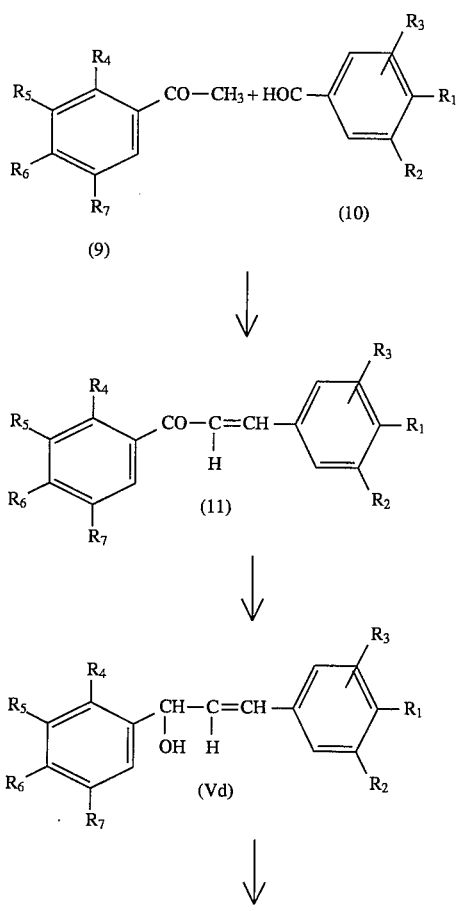

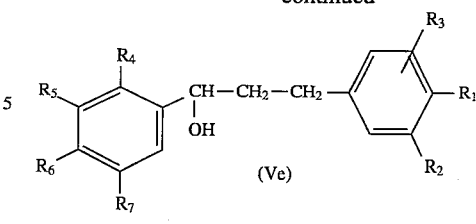

(Ve)

By a Mitsunobu type reaction starting with (Vb), (Vd) or (Ve) alcohols the azido derivative is obtained that can be transformed into an amino derivative.

By reaction of an anhydride or an acid chloride on the amino derivative, the corresponding amide is obtained.

In the case where the radical X is read in an inverse manner with respect to the preceding schemes resulting in compounds (Va), (Vb), (Vd) or (Ve), the compounds are obtained by the reactions described in these schemes by using starting products having the appropriate substituents.

When X represents a di- or trihydroxylated radical, the compounds of formula (V) are obtained by epoxidation of corresponding ethylenic compounds and opening of the epoxy function in an alkaline medium or in the presence of a hydride;

the aromatic retinoid imine derivatives described in French patent application 91-05883 having general formula (VI):

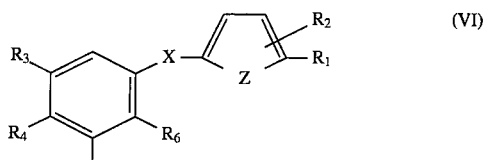

wherein $R_1$ represents hydrogen, OH, $—CH_3$, $—CH_2OH$, $—COR_7$, $—CH(OH)CH_3$, $—CH_2OCOR_8$, $—SO_2R_9$, $—SOR_9$ or $—SR_9$, $R_7$ represents hydrogen, OH, $—OR_{10}$,

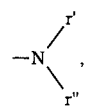

lower alkyl, monohydroxyalkyl, polyhydroxyalkyl or a sugar residue, $R_8$ represents a linear or branched alkyl having 1–20 carbon atoms, alkenyl having 2–20 carbon atoms or a sugar residue, $R_9$ represents OH, lower alkyl or

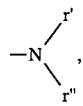

$R_{10}$ represents alkyl having 1–20 carbon atoms or alkenyl having 2–20 carbon atoms, r' and r", each independently, represent hydrogen, lower alkyl, aryl, aralkyl, an amino acid residue, a sugar residue, an aminated sugar residue or a heterocycle when r' and r" are taken together form a heterocycle, $R_2$ and $R_6$ represent hydrogen, OH, lower alkyl, alkoxy having 1-6 carbon atoms, fluorine, chlorine or $CF_3$, $R_3$ and $R_5$ represent $\alpha,\alpha'$-disubstituted alkyl having 4–12 carbon atoms or mono or polycyclic cycloalkyl having 5–12 carbon atoms whose linking carbon is trisubstituted, $R_4$ represents hydrogen, OH, alkoxy having 1–6 carbon atoms, $\alpha,\alpha'$-disubstituted alkyl having 4–12 carbon atoms, $R_3$ and $R_4$ or $R_4$ and $R_5$ taken together can form, with the adjacent benzenic nucleus, a ring having 5 or 6 carbon atoms substituted by 2–6 methyl groups, Z represents an atom of oxygen or sulfur, the divalent radical —CH=$CR_{11}$— or the divalent radical —N=$CR_{12}$—, $R_{11}$ represents hydrogen, OH or lower alkyl, $R_{12}$ represents hydrogen or lower alkyl, X is chosen from among the radicals:

(i) $-CR_{13}-N-$, (ii) $-N=CR_{13}-$, (iii) $\begin{array}{c} -C-NR_{14}- \\ \parallel \\ N-R_{15} \end{array}$ and (iv) $\begin{array}{c} -NR_{14}-C- \\ \parallel \\ N-R_{15} \end{array}$, $R_{13}$ represents $R_{16}$, $OR_{16}$, —$SR_{16}$ or

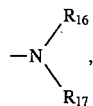

$R_{16}$ and $R_{17}$ represent hydrogen, lower alkyl, lower fluoroalkyl, alkenyl having 2–6 carbon atoms, alkynyl having 2–6 carbon atoms, aryl or aralkyl, $R_{14}$ represents lower alkyl, $R_{15}$ represents lower alkyl or lower fluoroalkyl, and in particular:
4-(N-methyl-5,6,7,8-tetrahydro-5,5,8,8-tetramethyl-2-naphthylcarboxamidino) benzoic acid and
4-(5,6,7,8-tetrahydro-5,5,8,8-tetramethyl-2-naphthylcarboxamidino) benzoic acid.

When X represents an imine bond with X=(i) the compounds (VI) are obtained by the reaction of a substituted benzaldehyde anhydrous solvent such as methylene chloride in the presence of a dehydrating agent, for example basic alumina.

When X represents an imine bond with X=(ii) the (VI) compounds are obtained by the reaction of a substituted aniline on an aromatic aldehyde substituted by an acid function which is protected in the form of an allylic ester under the same conditions set forth above.

When X represents an imidate, thioimidate or amidine bond, with X=(i), the (VI) compounds are prepared in accordance with the following reaction scheme:

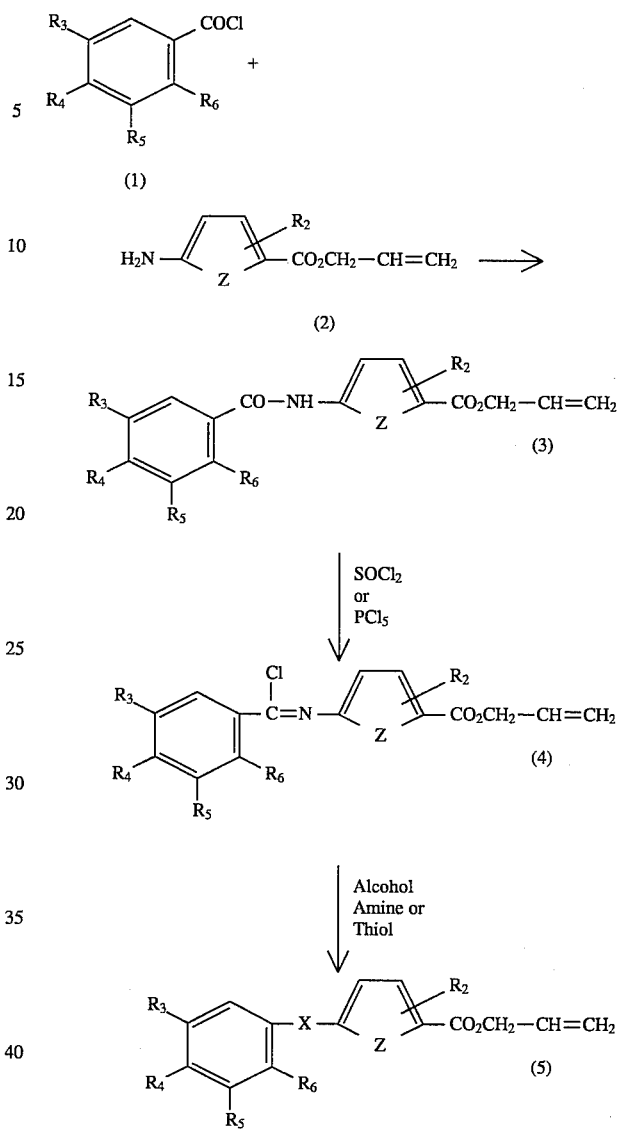

The first step consists in reacting in an anhydrous medium, in an organic solvent such as tetrahydrofuran or methylene chloride, containing a tertiary amine (pyridine or triethylamine) an activated form of a substituted benzoic acid, for example, an acid chloride (1) or a mixed anhydride on an allyl para-amino benzoate, optionally substituted, (2). The reaction is carried out at ambient temperature with stirring.

The amide (3) thus obtained is converted into the iminochloride (4) by the action of thionyl chloride, phosphorus pentachloride or phosgene.

By the reaction of compound (4) with an amine, an alcohol or a thiol in the presence of a tertiary amine and an alkaline hydride in an organic solvent such as tetrahydrofuran or methylene chloride, the compound of formula (5) is obtained.

When X represents an imidate, thioimidate or amidine bond with X=(ii) the preparation is carried out in the same manner as before by starting with the following compounds (6) and (7):

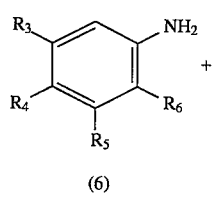

(6)

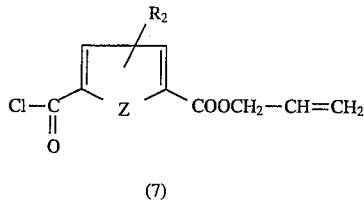

(7)

Passage of the ester to the free acid can be effected in the 4 cases above by means of a catalyst, such as certain transition metal complexes, for example, tetrakis triphenyl phosphine palladium (0) in the presence of a secondary amine or the sodium salt of diethyl malonate.

When X represents an amidine bond corresponding to formulas (iii) and (iv) the synthesis is carried out in accordance with the known Puiner process by condensing a substituted aniline on an aromatic nitrile.

The sterols useful in the composition of the present invention are those which are capable of inhibiting the biosynthesis of cholesterol. By "sterol" is meant compounds having the hydrocarbon squelette of cholesterol or lanosterol, and carrying besides at least one alkylated, oxygenated and/or nitrated substituent, and/or at least one unsaturation.

It is known that in man, for example, cholesterol is synthesized principally in the liver and intestine, but also in other organs, one of which is the skin. The departure point is acetyl coenzyme A (abbreviated acetyl CoA) which gives, by a reaction, acetoacetyl CoA, which, by reaction with another molecule of acetyl CoA, furnishes beta-hydroxy betamethylglutaryl CoA (abbreviated HMG CoA). These reactions are catalyzed by HMG CoA synthetase. The HMG CoA is reduced in mevalonic acid by the HMG CoA reductase. The mevalonic acid, on reaction with 3 ATP, fixes three phosphoryls and the compound obtained is transformed by decarboxylation into isopentenyl pyrophosphate. This latter compound isomerizes, under the action of an isomerase, into dimethylallyl pyrophosphate. On reaction of two molecules of isopentenyl pyrophosphate and one molecule of dimethylallyl pyrophosphate, a trimer, the farnesil pyrophosphate, is obtained in passing by the intermediary of a dimer (geranyl pyrophosphate). Two molecules of the trimer condense to form a hexamer squalene. By a complex cyclization reaction, in which intervenes principally 2,3-oxydosqualene cyclase, squalene transforms into 24,25-dihydrolanosterol then into lanosterol. The lanosterol is finally transformed into 14-desmethyl lanosterol which, on the loss of two methyls at position 4, gives zymosterol which isomerizes into cholesta-7,24-dienol, then into desmosterol. On reduction of the 24–25 double bond, cholesterol is finally obtained.

The sterols useful in the composition of the present invention are those which are capable of inhibiting the biosynthesis of cholesterol at any stage. It can be a question principally of inhibitors of HMG CoA reductase, inhibitors of 2,3-oxydosqualene cyclase, inhibitors of the metabolism of the 24,25-dihydrolanosterol, inhibitors of the conversion of lanosterol into demosterol or inhibitors of the conversion of desmosterol into cholesterol.

Among the inhibitors of HMG CoA reductase, mention can principally be made of: sterol carrying on the cholesterol structure or on a derived structure, at least one oxygenated substituent other than hydroxyl in position 3. The oxygenated substituent can be, for example, a hydroxyl, an oxo, an epoxy, a peroxide or a carbonyl. This substituent can be, for example, in position 4, 7, 14, 15, 20, 22, 24, 25 or 26. Mention can also be made, as an example, of 25-hydroxycholesterol.

Among the inhibitors of HMG CoA reductase mention of 6-nitrocholesterol can also be made.

Among the inhibitors of 2,3-oxydosqualene cyclase, mention can be made of, for example, 2-aza-2,3-dihydrosqualene or its derivatives, and N-[(1,,5,9)-trimethyldecyl]-4α,10-dimethyl-8-aza-trans-decal- 3β-ol.

Among the inhibitors of the metabolism of 24,25-dihydrolanosterol, mention can be made of certain unsaturated and oxygenated derivatives in position 8–9 of the lanosterol and in particular:

7-oxolanost-8-en-3β-ol,

3β-acetoxylanost-8-en-7-one and 7-oxolanost-5,8,11-trien-3β-ol.

Among the inhibitors of the conversion of demosterol into cholesterol, mention can principally be made of 20,25-diazacholesterol.

Among the inhibitors of the biosynthesis of cholesterol at a stage posterior to the biosynthesis of lanosterol, in accordance with the metabolic method lanosterol→cholesterol, mention can principally be made 22-oximino cholesterol.

In the composition of the present invention, the retinoid is generally present in an amount ranging from 0.0001 to 50 percent by weight relative to the total weight of the composition, and the ratio of the molar concentration of the sterol to the molar concentration of the retinoid can vary from 0.1 to 10.

The composition of the invention contains, other than the active ingredients mentioned above, a pharmaceutical vehicle compatible with an administration by a topical method (skin and mucous), ocular or systemic.

The two constituents of the synergistic combination can also be administered separately, by the same method or by different methods, and the invention also has for an object a composition in two parts comprising, assembled in an appropriate pack, on the one hand at least one retinoid, such as defined above, in an appropriate container and, in a second container, at least one sterol which is an inhibitor of the biosynthesis of cholesterol. This two-part composition also contains a mode of use recommending simultaneous or sequential administration of the two active principles.

For topical application, the pharmaceutical or cosmetic compositions of the invention comprise the vehicles and ingredients required to provide the composition, for example, in the form of ointments, creams, milks, pomades, powders, impregnated pads, solutions, gels, sprays, shampoos, washing lotions or even suspensions, microspheres or nanospheres, lipidic or polymeric vesicles or polymeric patches.

For ocular administration, the composition of the invention is provided in the form of eyewashes.

For buccal administration, the composition of the invention is provided in the form of a solution, suspension, gel, paste, lipidic or polymeric vesicles.

In the compositions for topical, ocular or buccal administration, the retinoid is present, for example, in amounts ranging from 0.0001 to 1 percent by weight based on the total weight of the composition. Generally the composition is applied 1–2 times per day on the area to be treated.

For systemic administration, the pharmaceutical compositions of the invention can be provided in the form of tablets, gelules, lozenges, syrups, dilutable powders, granules, microspheres, nanospheres, lipidic or polymeric vesicles, emulsions, suspensions or solutions for administration orally, by perfusion or by injection.

In the compositions administered orally, the retinoid is generally present in an amount ranging from 0.01 to 50 percent by weight based on the total weight of the composition.

In the compositions administered by perfusion or by injection the retinoid is generally present in an amount ranging from 0.0001 to 1 percent by weight based on the total weight of the composition.

The invention also has for an object the use, in combination, of at least one retinoid and at least one sterol, in the preparation of a pharmaceutical or cosmetic composition intended principally for the treatment or correction of epidermic keratinization disorders, any other disorder or any other functional defect or excess of epidermic or epithelial proliferation, and/or disorders of the sebaceous function. The composition thus prepared can serve to treat the disorders mentioned above, having or not an inflammatory and/or immunoallergic component, comprising conjunctive tissue degeneration disorders and benign or malignant tumors, to combat against skin aging, to favor cicatrization or to improve the appearance of the skin of persons exhibiting keratinization disorders or suffering from seborrhea.

In particular, the combination described in the present invention is intended:

for the treatment of dermatologic ailments linked to a keratinization disorder causing differentiation and proliferation and principally for treating common ache, comedons, polymorphs, nodulokystic acne, conglobuta, senile acne, secondary acne such as solar, medicinal and professional acne;

for the treatment of other types of keratinization disorders, principally ichthyoses, ichthyosiform conditions, Darier malady, palmoplantary keratodermies, leucophasies and leucoplasiform conditions as well as lichen;

for the treatment of dermatologic ailments linked to a keratinization disorder having an inflammatory and/or immunoallergic component and principally, all forms of psoriasis, be they cutaneous, mucous or ungual, and even psoriasic rheumatism, or again cutaneous atopies, such as eczema;

for the treatment of all cutaneous proliferations, benign or malignant, that are of viral origin such as common warts, plane warts and epidermodysplasie verruciform, or that are induced by ultraviolet radiations as, for example, in the case of baso epithalioma and cellular spino, in the treatment of cancerous or precancerous situations, in particular at the cutaneous level;

for the treatment of other dermatologic disorders such as blistery dermatoses and collagen maladies;

for combatting against aging of the skin, be it photoinduced or chronological or, to reduce pigmentation and actinic keratoses;

to prevent or heal scars of epidermic and/or dermic atrophy, induced by local or systemic corticosteroids, or any other form of cutaneous atrophy;

ta favor cicatrization;

for the treatment of certain ophthalmologic disorders, principally corneopathies;

to combat against disorders of the sebaceous function such as hyperseborrhea of acne or simple seborrhea;

for the repair of changes of collagenic and dermic elastic fibers, such as growth red marks, post-corticoid red marks and red marks during pregnancy. In this latter case, the treatment should be effected after the pregnancy;

to combat against degenerative or destructive ailments of inflammation of paradont and particularly gingivitis and paradontoclasies.

The compositions of the invention are also useful in the cosmetic field, in particular in body hygiene, and also capillary hygiene (action against seborrhea).

The following nonlimiting examples illustrate the invention.

EXAMPLES OF FORMULATIONS

Examples 1 and 2

Lotions

The following lotions were prepared:

Example 1

| | |
|---|---|
| Polyethylene glycol 400 | 49.850 g |
| Ethanol, 95% | 50.000 g |
| 2-(5,6,7,8-tetrahydro-5,5,8,8-tetramethyl-2-naphthyl)-5-benzimidazole carboxylic acid | 0.025 g |
| 25-hydroxy cholesterol | 0.075 g |
| Butylhydroxytoluene | 0.050 g |

Example 2

| | |
|---|---|
| Polyethylene | 59.89 g |
| Ethanol, 95% | 30 g |
| Isopropanol | 10 g |
| Butylhydroxytoluene | 0.05 g |
| Retinoic acid | 0.01 g |
| 25-hydroxy cholesterol | 0.05 g |

These lotions are applied on the skin, twice each day.

Examples 3 and 4

Gels

The following gels were prepared:

Example 3

| | |
|---|---|
| Hydroxypropylcellulose | 2.50 g |
| Ethanol, 95% | 97.41 g |
| Butylhydroxytoluene | 0.05 g |
| Retinoic acid | 0.01 g |
| 25-hydroxy cholesterol | 0.03 g |

Example 4

| | |
|---|---|
| Isopropyl myristate | 89.90 g |
| Colloidal silica | 10 g |
| a-tocopherol | 0.025 g |
| Retinoic acid | 0.025 g |
| 25-hydroxy cholesterol | 0.05 g |

These gels are applied to the affected areas of the skin twice each day.

Example 5

Water-In-Oil Emulsion

The following emulsion is prepared by dissolving hot (60°–70° C.) under an inert atmospheres and with mechanical stirring, on the one hand methyl parahydroxybenzoate in distilled water and on the other hand propyl parahydroxybenzoate in eucerin. While maintaining the temperature and remaining under an inert atmosphere, the aqueous part is then slowly emulsified in the eucerin with mechanical stirring. The temperature is permitted to lower to 40° C. before incorporating out of contact of light and with stirring the α-tocopherol, 25-hydroxy cholesterol, and then retinoic acid:

| | |
|---|---|
| Anhydrous eucerin | 40 g |
| Methyl parahydroxybenzoate | 0.075 g |
| Propyl parahydroxybenzoate | 0.075 g |
| α-tocopherol | 0.050 g |
| Distilled water | 59.70 g |
| Retinoic acid | 0.025 g |
| 25-hydroxy cholesterol | 0.075 g |

Anhydrous eucerin is a mixture of emulsive lanolin alcohols, waxes and raffinated oils with a hydrocarbon base, sold by BDF.

Examples 6 and 7

Oil-In-Water Emulsions

The following emulsions are prepared by dissolving hot (70° C.) under an inert atmosphere, on the one hand, liposoluble preservatives in a melted mixture of fatty bodies and emulsifying agents and on the other hand, methyl parahydroxybenzoate in distilled water. While maintaining the temperature and while remaining under an inert atmosphere, the lipid portion is then emulsified in the aqueous portion with mechanical stirring. The temperature is permitted to return to 40° C. before incorporating out of contact of light and with stirring the 25-hydroxy cholesterol, and then the retinoic acid.

Example 6

| | |
|---|---|
| Sodium lauryl sulfate | 1.00 g |
| 1,2-propanediol | 10.00 g |
| 1-hexadecanol | 18.00 g |
| Propyl parahydroxybenzoate | 0.075 g |
| Methyl parahydroxybenzoate | 0.075 g |
| Butyl hydroxytoluene | 0.050 g |
| Distilled water | 70.76 g |
| Retinoic acid | 0.010 g |
| 25-hydroxy cholesterol | 0.030 g |

Example 7

| | |
|---|---|
| Glyceryl stearate | 15.00 g |
| Sorbitan monostearate | 4.00 g |
| Sorbitan monostearate polyoxyethylenated with 20 moles of ethylene oxide | 1.00 g |
| 2-octyldodecanol | 10.00 g |
| Methyl parahydroxybenzoate | 0.15 g |
| Distilled water | 69.805 g |

-continued

| | |
|---|---|
| Butylhydroxytoluene | 0.01 g |
| Retinoic acid | 0.01 g |
| 25-hydroxycholesterol | 0.025 g |

The emulsions of Examples 5 to 7, which constitute creams, can be applied on the affected areas of the skin, twice each day.

Example 8

Gel-Cream

| | |
|---|---|
| Retinol palmitate | 0.050 g |
| 25-hydroxy cholesterol | 0.050 g |
| Hydrogenated soy lecithin | 5.000 g |
| α-tocopherol | 0.005 g |
| Methyl parahydroxybenzoate | 0.100 g |
| Propyl parahydroxybenzoate | 0.050 g |
| BHT | 0.050 g |
| Carboxy vinyl polymer (Carbopol 940) | 0.500 g |
| NaOH, 5% sufficient for pH = 7.0 | |
| Sterile water, sufficient amount for | 100.000 g |

Example 9

Gingival Gel

| | |
|---|---|
| Compound 1* | 0.025 g |
| 6-nitrocholesterol | 0.075 g |
| Hydroxypropyl cellulose | 2.500 g |
| Methyl parahydroxybenzoate | 0.150 g |
| Propyl parahydroxybenzoate | 0.050 g |
| Propylene glycol | 5.000 g |
| Sterile water, sufficient for | 100.000 g |

*Compound 1: 2-(5,6,7,8-tetrahydro-5,5,8,8-tetramethyl-2-naphthyl)-5-benzimidazole carboxylic acid

Activity of the Compounds on the Formation of Cornified Envelopes (CE) in Human Keratinocyte Cultures Transformed By SV-40

The activity of the combination between retinoid and sterol on the formation of corneal envelopes has been evaluated according to the method described by S. Michel et coll. in Models Dermatol, Maibach and Lowe Eds, Karger, Basel, Vol. 4, p. 40–44 (1989)

Example I

Retinoic Acid and 25-Hydroxy Cholesterol

| Compounds | Doses | Inhibition of the formulation of CE |
|---|---|---|
| Retinoic acid | 0.01 μM | 0%–10% |
| | 1.00 μM | 80%–100% |
| 25-OH cholesterol | 0.026 μM | 0%–10% |
| Retinoic acid + 25-OH cholesterol | 0.01 μM + 0.026 μM | 80%–100% |

Example II

Compound 1* and 25-Hydroxy Cholesterol

| Compounds | Doses | Inhibition of the formulation of CE |
| --- | --- | --- |
| Compound 1 | 0.50 μM | 10% |
| 25-OH cholesterol | 1.28 μM | 55% |
| Compound 1 + 25-OH cholesterol | 0.50 μM + 1.28 μM | 100% |
| Compound 1 + 25-OH cholesterol | 0.25 μM + 0.64 μM | 100% |

*Compound 1: 2-(5,6,7,8-tetrahydro-5,5,8,8-tetramethyl-2-naphthyl)-5-benzimidazole carboxylic acid

We claim:

1. A pharmaceutical or cosmetic composition comprising in combination at least one retinoid capable of inhibiting the expression of membranal transglutaminase, said retinoid not having a heterocycle moiety, and at least one sterol which functions as an inhibitor of the biosynthesis of cholesterol.

2. The composition of claim 1 wherein said retinoid is selected from the group consisting of all-trans or 13-cis retinoic acid, (all-E)-9-(4-methoxy-2,3,6-trimethylphenyl)-3,7-dimethyl-2,4,6,8-nonatetraenoic acid, (E,E,E)-7-(2,3,-dihydro-1,1,3,3-tetramethyl-1H-inden-5-yl)-3,7-dimethyl-2,4,6-octatrienoic acid, (E,E,E)-7-(5,6,7,8-tetrahydro-5,5,8,8-tetramethyl-2-naphthalenyl)- 3,7-dimethyl-2,4,6-octatrienoic acid, (E)-4-[(2,3,-dihydro-1,1,3,3-tetramethyl-1H-inden-5-yl)-1-propenyl] benzoic acid, (E)-4-[2-(5,6,7,8-tetrahydro-5,5,8,8-tetramethyl-2-naphthalenyl)- 1-propenyl] benzoic acid, (E)-4-[2-(5,6,7,8-tetrahydro-3-methyl-5,5,8,8-tetramethyl-2-naphthalenyl)- 1-propenyl] benzoic acid, 2-(5,6,7,8-tetrahydro-5,5,8,8-tetramethyl-2-naphthyl)-6-naphthalene carboxylic acid, (E)-4-[2-(5,6,7,8-tetrahydro-5,5,8,8-tetramethyl-2-naphthalenyl)- 1-propenyl] benzene sulfonic acid, (E,E)-4-[2-methyl-4-(2,6,6-trimethyl-1-cyclohexen-1-yl)-1,3-butadienyl] benzoic acid, (E,E)-4-[4-methyl-6-(2,6,6-trimethyl-1-cyclohexen-1-yl)-1,3,5-hexatrienyl] benzoic acid, (E)-6-[2-(2,6,6-trimethyl-1-cyclohexen-1-yl)-ethenyl]-2-naphthalene carboxylic acid, (E)-4-[2-(5,6,7,8-tetrahydro-8,8-dimethyl-2-naphthalenyl)-1-propenyl] benzoic acid, 4-[(5,6,7,8-tetrahydro-5,5,8,8-tetramethyl-2-naphthenyl)ethynyl] benzoic acid, (E)-4-[2-(5,6,7,8-tetrahydro-3-methyl-5,5,8,8-tetramethyl-2-naphthalenyl)- 1-propenyl] benzoic acid, 4-(5,6,7,8-tetrahydro-5,5,8,8-tetramethyl-2-naphthalenylcarbamoyl) benzoic acid, 4-(5,6,7,8-tetrahydro-5,5,8,8-tetramethyl-2-naphthamido) benzoic acid, (E)-4-[3-(3,5-ditert-butylphenyl)-3-oxo-1-propenyl] benzoic acid, 6-[(5,6,7,8-tetrahydro-5,5,8,8-tetramethyl-2-naphthalenyl) ethynyl] 3-pyridine carboxylic acid, 2-(5,6,7,8,-tetrahydro-5,5,8,8-tetramethyl-2-naphthyl)-6-benzo(b) thiophene carboxylic acid, 4-(5,6,7,8-tetrahydro-5,5,8,8-tetramethyl-2-anthracenyl) benzoic acid, 6-[3-(1-adamantyl)-4-methoxyphenyl]-2-naphthoic acid, 4-[3-(1-adamantyl)-4-methoxybenzamido] benzoic acid, 4-[3-(1-adamantyl)-4-methoxy benzoylthio] benzoic acid, 4-[3-(1-adamantyl)-4-methoxy benzoyloxy] benzoic acid, 2-(5,6,7,8-tetrahydro-5,5,8,8-tetramethyl-2-naphthyl)-6-carbonyl naphthalene carboxylic acid, trans-(5,5,8,8-tetramethyl-5,6,7,8-tetrahydro-2-naphthyl)-4-carbonyl-α-methyl cinnamic acid, the vitamin A or retinol, as well as its esters, such as the acetate, propionate or palmitate of retinol, aldehyde of vitamin A or retinal 4-[3-(1-adamantyl)-4-methoxybenzoyloxy]-2-fluorobenzoic acid, 4-[3-(1-adamantyl)-4-methoxybenzoyloxy]-2-methylbenzoic acid, 4-[3(1-adamantyl)-4-methoxybenzoyloxy]-2-hydroxybenzoic acid, 4-[5-(1-adamantyl)-2-fluoro-4-methoxybenzoyloxy] benzoic acid, 4-[3,5-di-tert.butyl-4-hydroxybenzoyloxy] benzoic acid, 4-[3-(1-adamantyl)-4-vinylbenzoyloxy] benzoic acid, 4-[3-(1-adamantyl)-4-ethylbenzoyloxy] benzoic acid, 4-[3-(1-adamantyl)-4-allyloxybenzoyloxy] benzoic acid, 4-[3-(1-adamantyl-4-methylthiobenzoyloxy] benzoic acid, 4-(5,6,7,8,-tetrahydro-5,5,8,8-tetramethyl-2-naphthylglyoxyloyloxy) benzoic acid, 4-(5,6,7,8-tetrahydro-5,5,8,8-tetramethyl-2-naphthoyloxymethyl) benzoic acid, 4-(3,5-di-tert.butyl-4-hydroxybenzoyloxymethyl) benzoic acid, 4-(3-tert-butyl-4-methoxybenzoyloxymethyl) benzoic acid, 4-(5,6,7,8-tetrahydro-5,5,8,8-tetramethyl-2-naphthoylmethyloxy) benzoic acid, 4-[1-(5,6,7,8-tetrahydro-5,5,8,8-tetramethyl-2-naphthoyloxy) ethyl] benzoic acid, 4-[[(5,6,7,8-tetrahydro-5,5,8,8-tetramethyl-2-naphthyl)ethyloxy] carbonyl] benzoic acid, 4-(5,6,7,8-tetrahydro-5,5,8,8-tetramethyl-2-naphthoylmethylamino) benzoic acid, 4-(5,6,7,8-tetrahydro-5,5,8,8-tetramethyl-2-naphthoyl formamido)benzoic acid, 4-(α-hydroxy-5,6,7,8-tetrahydro-5,5,8,8-tetramethyl-2-naphthylacetamido) benzoic acid, 4-(α-fluoro-5,6,7,8-tetrahydro-5,5,8,8-tetramethyl-2-naphthylacetamido) benzoic acid, 6-[3-(1-adamantyl)-4-(2,3-dihydroxypropyloxy) phenyl]-2-naphthoic acid, 6-[3-(1-adamantyl)-4-(3-hydroxypropyloxy)phenyl]-2-naphthoic acid, 6-[3-(1-adamantyl)-4-acetoxymethylphenyl]-2-naphthoic acid, 6-[3-(1-adamantyl)-4-methoxycarbonylphenyl]-2-naphthoic acid, 6-[3-(1-adamantyl)-4-methoxycarbonylethylphenyl]-2-naphthoic acid, 6-[3-(1-adamantyl)-4-(2-hydroxypropyl) phenyl]-2-naphthoic acid, 2-hydroxy-4-[2-hydroxy-2-(5,6,7,8-tetrahydro-5,5,8,8-tetramethyl- 2-naphthyl) ethoxy] benzoic acid, methyl 2-hydroxy-4-[2-hydroxy-2-(5,6,7,8,-tetrahydro-5, 5,8,8-tetramethyl-2-naphthyl) ethoxy] benzoate, 2-hydroxy-4-[2-hydroxyimino-2-(5,6,7,8-tetrahydro-5,5, 8,8-tetramethyl- 2-naphthyl) ethoxy]benzoic acid, 2-acetyloxy-4-[2-acetyloxy-2-(5,6,7,8-tetrahydro-5,5,8, 8-tetramethyl- 2-naphthyl) ethoxy] benzoic acid, 2-hydroxy-4-[2-acetyloxy-2-(5,6,7,8-tetrahydro-5,5,8,8-tetramethyl- 2-naphthyl) ethoxy] benzoic acid, 2-acetyloxy-4-[2-hydroxy-2-(5,6,7,8-tetrahydro-5,5,8,8-tetramethyl- 2-naphthyl) ethoxy] benzoic acid, 4-(N-methyl-5,6,7,8-tetrahydro-5,5,8,8-tetramethyl-2-naphthylcarboxaminidino) benzoic acid, 4-(5,6,7,8-tetrahydro-5,5,8,8-tetramethyl-2-naphthylcarboxamidino) benzoic acid.

3. The composition of claim 1 wherein said sterol is an inhibitor of 3-hydroxy-3-methylglutarylcoenzyme A reductase.

4. The composition of claim 3 wherein said sterol is 6-nitrocholesterol.

5. The composition of claim 3 wherein said sterol is cholesterol substituted with at least one oxygen-containing substituent selected from the group consisting of hydroxyl, oxo, epoxy, peroxide and carbonyl, in position 4, 7, 14, 15, 20, 22, 24, 25 or 26.

6. The composition of claim 4 wherein said sterol is 25-hydroxycholesterol.

7. The composition of claim 1 wherein said sterol is an inhibitor of 2,3-oxydosqualene cyclase.

8. The composition of claim 7 wherein said sterol is selected from the group consisting of 2-aza-2,3-dihydrosqualene and N-[(1,5,9)-trimethyldecyl]-4α,10-dimethyl-8-aza-trans-decal-3β-ol.

9. The composition of claim 1 wherein said sterol is an inhibitor of the metabolism of 24,25-dihydrolanosterol.

10. The composition of claim 9 wherein said sterol is selected from the group consisting of 7-oxolanost-8-en-3β-ol, 3β-acetoxylanost-8-en-7-one and 7-oxolanost-5,8,11-trien-3β-ol.

11. The composition of claim 1 wherein said sterol functions as an inhibitor of the conversion of lanosterol into cholesterol.

12. The composition of claim 1 wherein said sterol functions as an inhibitor of the conversion of lanosterol into desmosterol.

13. The composition of claim 1 wherein said sterol functions as an inhibitor of the conversion of desmosterol into cholesterol.

14. The composition of claim 11 wherein said sterol is selected from the group consisting of 22-oximino cholesterol and 20,25-diazacholesterol.

15. The composition of claim 12 wherein said sterol is selected from the group consisting of 22-oximino cholesterol and 20,25-diazacholesterol.

16. The composition of claim 13 wherein said sterol is selected from the group consisting of 22-oximino cholesterol and 20,25-diazocholesterol.

17. The composition of claim 1 wherein said retinoid is present in an amount ranging from 0.0001 to 50 percent by weight based on the total weight of said composition.

18. The composition of claim 1 wherein said retinoid is present in an amount ranging from 0.0001 to 1 percent by weight based on the total weight of said composition.

19. The composition of claim 1 wherein said retinoid is present in an amount ranging from 0.01 to 50 percent by weight based on the total weight of said composition.

20. The composition of claim 18 wherein the ratio of the molar concentration of the sterol to the molar concentration of said retinoid is in the range of 0.1 to 10.

21. The composition of claim 19 wherein the ratio of the molar concentration of the sterol to the molar concentration of said retinoid is in the range of 0.1 to 10.

22. The composition of claim 1 which also contains a topical, ocular or buccal administrable component present in an amount ranging from 0.0001 to 1 percent by weight based on the total weight of said composition.

23. The composition of claim 1 in the form of two parts, assembled in a two container pack, one of said containers containing said retinoid defined in claim 1, the other container containing said sterol defined in claim 1.

* * * * *